United States Patent [19]

Chuang et al.

[11] Patent Number: 4,961,921
[45] Date of Patent: Oct. 9, 1990

[54] NON-AEROSOL PUMP SPRAY COMPOSITIONS

[75] Inventors: Jui-Chang Chuang, Wayne; Edward Walls, Jr., Cranford; Stephen C. Johnson, Newton, all of N.J.

[73] Assignee: GAF Chemicals Corporation, Wayne, N.J.

[21] Appl. No.: 341,322

[22] Filed: Apr. 21, 1989

[51] Int. Cl.⁵ .............................................. A61K 7/00
[52] U.S. Cl. ...................................... 424/47; 424/70; 424/71; 424/81
[58] Field of Search ........................ 424/47, 70, 71, 81

[56] References Cited

U.S. PATENT DOCUMENTS 4,543,249  9/1985  Nelson ................................. 424/70
4,689,379  8/1987  Chuang ................................ 424/47

*Primary Examiner*—Merrell C. Cashion, Jr.
*Assistant Examiner*—P. L. Prater
*Attorney, Agent, or Firm*—Walter Katz; Marilyn J. Maue; Joshua J. Ward

[57] ABSTRACT

Non-aerosol pump hair spray compositions herein are applied as a fine spray mist, without nozzle clogging, and dried rapidly, to provide superior hair holding power. The compositions includes a hair fixative resin which is a terpolymer of a vinyl ester, an alkyl maleate half ester, and an acrylate ester of a saturated, hydroxylated bicyclic hydrocarbon, in an amount between 6 and 20% solids, and at a relative viscosity of from 1.10 to below 1.30.

11 Claims, No Drawings

NON-AEROSOL PUMP SPRAY COMPOSITIONS

BACKGROUND OF THE INVENTION

1. Field of the Invention

This invention relates to a non-aerosol, pump hair spray composition which can be applied as a fine spray mist, which dries rapidly, and which provides superior hair holding power, without nozzle clogging.

2. Description of the Prior Art

Aerosol hair spray products contain a hair spray composition which includes a hair fixative resin and a volatile propellant. These cosmetic products apply the resin as a fine, dispersed spray which exhibits excellent hair holding power. However, the propellants used therein are known to adversely affect the ozone layer of the atmosphere. For this reason, it is desired to provide non-aerosol, pump hair spray compositions which exhibit the same advantageous properties as aerosol hair sprays.

Non-aerosol hair spray compositions are applied by means of a pressure actuated pump nozzle. However, commercially available pumps for non-aerosol application have restricted nozzle orifices which limits its use to resin compositions having a low solids content. Unfortunately, the restriction on resin solids content reduces the holding power of the hair spray. Furthermore, if the solids content of the resin composition is increased, the spray pattern becomes streamed rather than sprayed. This effect is caused by the inability of the nozzle to effectively break up hair spray compositions of high solids content. Furthermore, nozzle clogging becomes evident if the solids content is increased. Accordingly, hair spray resins used in present non-aerosol hair spray products generally are present at about a 5% solids level, which enables only relatively weak hair holding power and poor curl retention.

Jui-Chang Chuang, in U.S. Pat. No. 4,689,379, described the preparation of terpolymeric hair fixative resins for use particularly in aerosol spray formulations. The terpolymer resin comprised a vinyl acetate/mono-$C_4$–$C_5$ alkyl maleate/isobornyl acrylate or methacrylate, preferably in a molar ratio of 1:0.75:0.1. The hair spray compositions included such resins in concentrations between 0.5% and about 10% solids, preferably 2.5%–5%, and required a relative viscosity (RV) of greater than 1.30, preferably 1.64 (K=48.5). A resin which had a relative viscosity of 1.07 (K=15) exhibited only very poor curl retention (Example 14).

Accordingly, it is an object of this invention to provide a non-aerosol pump hair spray composition and cosmetic product which can be applied to the user as a fine spray mist, which dries rapidly, and which has superior hair holding power, without nozzle clogging.

A particular object herein is to provide a hair spray composition having a high solids content hair fixative resin which can be applied through a nozzle pump as a fine mist and which exhibits excellent hair holding power.

SUMMARY OF THE INVENTION

What is described herein is a non-aerosol hair spray composition capable of being applied by the user as a fine spray mist which dries rapidly and provides effective hair holding power without nozzle clogging. The composition includes from about 6 to 20% of a hair fixative resin which is a terpolymer of a vinyl ester, a water insoluble or water miscible alkyl maleate half ester and an acrylate or methacrylate ester of a saturated hydroxylated bicyclic hydrocarbon having a relative viscosity of from 1.10 to below 1.30, the carboxyl groups of which are 10 to 100% neutralized with a water soluble base and about 65 to 94% of ethanol solvent.

DETAILED DESCRIPTION OF THE INVENTION

In accordance with the present invention, the resins utilized in the non-aerosol pump hair spray compositions are terpolymer resins described in detail in U.S. Pat. No. 4,689,379. The terpolymer resin is a random or alternating structure comprising essentially a vinyl ester, a water insoluble or water miscible alkyl maleate half ester and an acrylate or methacrylate ester of a saturated hydroxylated bicyclic hydrocarbon in a molar ratio of about 1:0.35–1:0.05–0.25.

Acrylate and/or methacrylate esters of isoborneol, exonorborneol and endo-norborneol are preferred and the isobornyl ester is the most preferred. The preferred bicyclic compounds are those having a hydrocarbon bridge and are generally defined by the formula

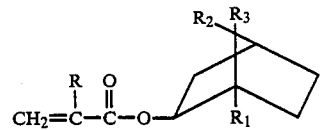

wherein each of R, $R_1$, $R_2$ and $R_3$ is hydrogen or methyl.

The molar ratio of vinyl ester to the bicyclic acrylate or methacrylate monomer in the terpolymer should be between about 4:1 and about 20:1. A particularly preferred molar ratio of vinyl acetate/mono-$C_4$ to $C_5$ alkyl maleate/isobornyl acrylate or methacrylate is about 1:0.6–0.8:0.08–0.12, e.g. 1:0.75:0.1.

Illustrative of the water insoluble or water miscible alkyl maleate half ester monomers of this invention are the propyl, butyl, pentyl, hexyl, heptyl, octyl, nonyl and decyl half esters; although the n-butyl and n-pentyl half esters are the most preferred.

Examples of the vinyl ester monomeric component are those containing 4 to 14 carbon atoms which include vinyl acetate, vinyl propionate, vinyl isobutyrate, vinyl butyrate, vinyl hexanoate, vinyl pivalate, vinyl laurate and vinyl neodecanoate, of which vinyl acetate is the most preferred.

The resins herein are prepared by a solution polymerization process which provides the resin within the requisite relative viscosity range and K values and solids content. The process comprises adding the monomers, individually or premixed in the above proportions in a suitable solvent for both the monomers and the terpolymer, for example, acetone, ethanol or mixtures thereof, wherein they are polymerized in the presence of a free radical initiator under conditions of agitation at a temperature of between about 40° and about 90° C., preferably between about 50° and about 70° C. The initiator can be added to the monomer mixture before or after the monomers have been charged into the solution medium. The reaction is carried out under an inert atmosphere which can be maintained by purging with nitrogen to eliminate air and oxygen.

The polymerization reaction is carried under constant agitation over a period of from about 4 to 24 hours, although usually 8 to 16 hours is sufficient to complete the reaction and form a terpolymer product. At this point, ethanol is added and acetone solvent is removed by distillation until the reactant temperature reaches about 60° to 90° C., preferably about 70° to 80° C. The terpolymer product has a relative viscosity of 1.10 to less than 1.30, preferably about 1.20, a K value in the range of 18 to 30, preferably about 27, and a resin solids content of about 40 to 80, preferably about 50% solids.

The terpolymeric resins thus prepared by solution polymerization with the predetermined relative viscosity range and molecular weights are employed as the active ingredient in a non-aerosol pump hair spray formulation and employed in a cosmetic product fitted with a suitable nozzle pump valve. The present resins are employed in concentrations between about 6 to 20% solids, preferably 8 to 15% solids. Such cosmetic products can be used over an extended period of time to generate fine spray mists without experiencing any nozzle clogging.

The hair treatment formulations herein include a solvent for the resin, such as a lower alcohol, e.g. ethanol, an aqueous ethanol solution, isopropanol and the like, etc. Generally aqueous ethanol is preferred and in an amount of about 65 to 94% of the formulation.

In preparing the hair treatment formulations, the terpolymers are at least 10% neutralized with a water soluble base to provide water solubility and shampoo removability, and preferably, about 50 to 100% neutralized. Examples of suitable water-soluble bases include ammonium hydroxide, sodium hydroxide, potassium hydroxide; mono-, di-, and tripropanolamine, dimethylstearamine, aminomethylpropanol, aminomethylpropanediol, or mixtures thereof. Water-soluble organic bases are preferred and aminomethylpropanol is especially preferred.

Improved results are obtained when plasticizer for the polymer is added to the formulation. When used, about 0.05 to 0.5 percent by weight, based on the weight of the copolymer, of either an ester or silicone plasticizer is added. Suitable ester plasticizers include isocetyl stearate, diisopropyl adipate, isohexyl laurate, isohexyl palmitate, and isocetyl stearate. Isocetyl stearate is preferred. Suitable silicones include dimethicone copolyol (Silicone Fluid SF-1066, General Electric Co.) which is the reaction product of dimethyl siloxane and ethylene oxide, propylene oxide and/or glycols. Some degree of plasticization is achieved by the water present in the compositions of the invention.

The formulations are charged into a suitable container and fitted with a pump valve. When operated through a pressure release nozzle, the formulations provides a fine spray mist and avoids nozzle clogging when the resins are employed within the predetermined relative viscosity range and solids content defined above.

Having thus generally described the invention, reference is now had to the following examples which provide specific and preferred embodiments but which are not to be construed as limiting to the scope of the invention as more broadly described above and in the appended claims. All parts given are by weight unless otherwise indicated.

EXAMPLE 1

This example illustrates the preparation of a vinyl acetate/mono-n-butyl maleate/isobornyl acrylate terpolymer having a predetermined molecular weight within the range of this invention. Polymerization is carried out in acetone followed by an exchange of acetone with ethanol.

Into a four-necked, one-liter resin kettle, fitted with a nitrogen inlet tube, a dropping-funnel, a thermometer, a reflux condenser and a mechanical agitator, was charged 103.2 g. of vinyl acetate (1.2 moles), 154.8 g. of mono-n-butyl maleate (0.9 mole) and 24.96 g. of isobornyl acrylate (0.12 mole). After charging 0.2653 g. of di-ethylhexyl peroxydicarbonate (Lupersol ® 223M75, 75% active) and 282.96 g. of acetone, the reactants were bubbled with nitrogen (150 ml/min.) for 15 minutes. The reactants then were heated gently under agitation (250 rpm) to 49° C. over 20 minutes and then to 58° C. over the next 10 minutes (mild reflux). The reaction was held at 58°-60° C. for 16 hours while adding 0.2653 g. of Lupersol ® 223M75 hourly. At this point, unreacted vinyl acetate was 0.90% by titration. Then 282.96 g. of SDA-40-2 ethanol (95%) was added. Acetone was removed by distillation until the reactant temperature was 74° C. The terpolymer has a resin solids of 50.4%, a relative viscosity of 1.28 and a K value of 32.

EXAMPLE 2

This example illustrates the preparation of a vinyl acetate/mono-n-butyl maleate/isobornyl acrylate terpolymer in ethanol having a desired molecular weight wherein the monomer concentration is varied during the polymerization.

Into a one-liter resin kettle, fitted with a nitrogen inlet tube, a thermometer, a reflux condenser and a mechanical agitator, was charged 103.2 g. of vinyl acetate (1.2 moles), 154.8 g. of mono-n-butyl maleate (0.9 mole) and 24.96 g. of isobornyl acrylate (0.12 mole). After adding 0.2653 g. of di-ethylhexyl peroxydicarbonate (Lupersol 223M75, 75% active) and 31.44 g. of ethanol, the reactants were purged with nitrogen (150 ml/min.) for 15 minutes. The reactants then were heated gently under agitation (250 rpm) to 49° C. for 20 minutes and then to 58° C. over the next 10 minutes. The reaction was held at 58°-60° C. for 20 hours while adding 0.2653 g. of Lupersol 223M75 hourly. During the polymerization, additional amounts of 39 g., 50 g. and 64 g. of ethanol were added at the end of second, fourth and sixth hour, respectively, to maintain the reactants at a stirrable viscosity. At the end of twentieth hour, unreactive vinyl acetate was determined by titration to be 0.70%. The clear, viscous terpolymer in ethanol had a resin solids of 67.2%, a relative viscosity of 1.17, and a K-value of 24.8.

EXAMPLE 3

This example illustrates the preparation of a vinyl acetate/mono-n-butyl maleate/isobornyl acrylate terpolymer in ethanol with the desired molecular weight, while the monomer concentration is kept at constant level during the course of polymerization.

Into a one-liter resin kettle, fitted with a nitrogen inlet tube, a thermometer, a reflux condenser and a mechanical agitator, was charged 103.2 g. of vinyl acetate (1.2 moles), 154.8 g. of mono-n-butyl maleate (0.9 mole) and 24.96 g. of isobornyl acrylate (0.12 mole). After adding 0.2653 g. of di-ethylhexyl peroxydicarbonate (Lupersol 223M75, 75% active) and 70.74 g. of ethanol, the reactants were bubbled with nitrogen (150 ml/min.) for 15 minutes. The reactants were heated gently under agitation (250 rpm) to 49° C. for 20 minutes and then to 58° C. over the next 10 minutes. The reaction was held at 58°-60° C. for 16 hours while adding 0.2653 g. of Lupersol 223M75 hourly. At this point, unreacted vinyl acetate was 1.0% by titration. Then 161.69 g. of SDA-40-2 ethanol was added. The clear, viscous terpolymer in ethanol has a resin solids of 46.6%, a relative viscosity of 1.20, and a K value of 19.9.

EXAMPLE 4

This example illustrates the preparation of a vinyl acetate/mono-n-butyl maleate/isobornyl acrylate in a mixture of acetone and ethnol to provide a molecular weight terpolymer within the range of this invention.

Into a one-liter resin kettle, fitted with a nitrogen inlet tube, a thermometer, a reflux condenser and a mechanical agitator, was charged 103.2 g. of vinyl acetate (1.2 moles), 154.8 g. of mono-n-butyl maleate (0.9 mole) and 24.96 g. of isobornyl acrylate (0.12 mole). After adding 0.2653 g. of di-ethylhexyl peroxydicarbonate (Lupersol 223M75, 75% active) and 36.91 g. of ethanol and 84.36 g. of acetone, the reactants were bubbled with nitrogen (150 ml/min.) for 15 minutes. The reactants were heated gently under agitation (250 rpm) to 49° C. for 20 minutes and then to 58° C. over the next 10 minutes (mild reflux). The reaction was held at 58°-60° C. for 20 hours while adding 0.2653 g. of Lupersol 223M75 hourly. At this point, unreacted vinyl acetate was 0.60% by titration. Then 246.05 g. of SDA-40-2 ethanol was added. Acetone was removed by distillation until the reactant temperature was 74° C. The clear, viscous terpolymer in ethanol had a resin solids of 60.7%, a relative viscosity of 1.24, and a K value of 30.0.

EXAMPLE 5

This example provides a representative formulations for a non-aerosol hair spray. The resins were dissolved in 95% ethanol and 100% neutralized with 2-amino-2-methyl-1-propanol (AMP).

|  | Formulation A Wt. (g) | Formulation B Wt. (g) |
|---|---|---|
| Terpolymer of Ex. 1 (50.4% solids) | 20 | 28 |
| Ethanol (95%) | 77.2 | 68.0 |
| AMP | 2.8 | 4.0 |

The above formulations were charged into a plastic container fitted with a Mistette II (Calmar) valve and sprayed on clean, virgin tresses. The spray patterns developed were fine dispersed mists which dried to non-tacky, clear, transparent film within about 8-12 seconds. Formulation A (10% resin solids) exhibited a curl retention of 85% after 30 minutes, 78% after 40 minutes, 75% after 60 minutes, and 70% after 80 minutes. Formulation B (14% resin solids) had curl retentions of 95%, 88%, 85% and 80%, after similar periods of time. Similar formulations with Gantrez ® ES-225 (GAF) permitted only a 5% solids level, which provided curl retention percentages of only 70%, 60%, 50% and 47%.

What is claimed is:

1. A non-aerosol pump hair spray composition capable of being applied by the user as a fine spray mist which dries rapidly and provides effective hair holding power without nozzle clogging consisting essentially of from about 6 to 20% by weight of a hair fixative resin which is a terpolymer of a vinyl ester, a water insoluble or water miscible alkyl maleate half ester and an acrylate or methacrylate ester of a saturated, hydroxylated, bicyclic hydrocarbon, having a relative viscosity of from 1.10 to below 1.30, the carboxyl groups of which are 10 to 100% neutralized with a water soluble base and about 65 to 94% ethanol or aqueous ethanol solvent.

2. A non-aerosol pump hair spray composition according to claim 1 comprising about 8-15% by weight of said terpolymer.

3. A non-aerosol pump hair spray according to claim 1 wherein said terpolymer has a relative viscosity of about 1.20.

4. A non-aerosol pump hair spray composition according to claim 1 wherein said vinyl ester is vinyl acetate and said acrylate or methacrylate monomer is isobornyl acrylate, isobornyl methacrylate or a mixture thereof.

5. The composition of claim 1 wherein said alkyl maleate half ester is mono-butyl maleate, mono-pentyl maleate, or a mixture thereof.

6. The composition of claim 1 wherein said terpolymer is vinyl acetate/mono-butyl maleate/isobornyl acrylate in a molar ratio of about 1:0.6-0.8:0.08-0.12.

7. A non-aerosol pump hair spray composition according to claim 1 additionally including about 0.05 to 0.5% by weight, based upon the terpolymer, of a plasticizer selected from a fatty acid ester or a silicone.

8. A non-aerosol pump hair spray composition according to claim 1 wherein said base is a water soluble organic base.

9. A non-aerosol pump hair spray composition according to claim 8 wherein said organic base is an organic amine.

10. A non-aerosal pump hair spray composition according to claim 9 wherein said organic amine is 2-amino-2-methyl-1-propanol or dimethylstearamine.

11. A non-aerosol pump hair spray composition according to claim 1 wherein said solvent is aqueous ethanol.

* * * * *